(12) United States Patent
Tenerz et al.

(10) Patent No.: US 6,648,810 B1
(45) Date of Patent: *Nov. 18, 2003

(54) MEDICAL DEVICE

(75) Inventors: Lars Tenerz, Uppsala (SE); Jonas Tirén, Uppsala (SE); Leif Smith, Uppsala (SE)

(73) Assignee: Radi Medical Technologies AB, Uppsala (SE)

( * ) Notice: Subject to any disclaimer, the term of this patent is extended or adjusted under 35 U.S.C. 154(b) by 436 days.

This patent is subject to a terminal disclaimer.

(21) Appl. No.: 09/708,665

(22) Filed: Nov. 9, 2000

(51) Int. Cl.[7] .................. A61N 5/00; A61M 25/00; H05H 35/00
(52) U.S. Cl. .................. 600/3; 600/435; 378/119
(58) Field of Search .................. 600/3, 435; 378/121, 378/122, 119, 65, 202, 200, 145, 163, 136, 142, 138, 130; 604/264, 20, 529; 404/4; 405/49

(56) References Cited

U.S. PATENT DOCUMENTS

| | | | |
|---|---|---|---|
| 3,714,786 A | * 2/1973 | Evans et al. .................. 405/49 |
| 4,279,252 A | * 7/1981 | Martin .................. 600/435 |
| 5,153,900 A | * 10/1992 | Nomikos et al. .................. 378/65 |
| RE34,421 E | * 10/1993 | Parker et al. .................. 378/121 |
| 5,303,283 A | * 4/1994 | Jedlitschka et al. .................. 378/202 |
| 5,422,926 A | * 6/1995 | Smith et al. .................. 378/121 |
| 5,428,658 A | * 6/1995 | Oettinger et al. .................. 378/119 |
| 5,566,221 A | * 10/1996 | Smith et al. .................. 378/145 |
| 5,729,583 A | * 3/1998 | Tang et al. .................. 378/122 |
| 5,854,822 A | 12/1998 | Chornenky et al. .................. 378/122 |
| 6,095,966 A | * 8/2000 | Chornenky et al. .................. 600/3 |
| 6,108,402 A | * 8/2000 | Chornenky .................. 378/119 |
| 6,514,192 B2 | * 2/2003 | Tiren .................. 600/3 |

FOREIGN PATENT DOCUMENTS

| | | |
|---|---|---|
| DE | 198 42 466 | 4/2000 |
| WO | 97/07740 | 3/1997 |
| WO | 98/48899 | 11/1998 |

* cited by examiner

Primary Examiner—Eric F. Winakur
Assistant Examiner—Nikita Veniaminov
(74) Attorney, Agent, or Firm—Foley & Lardner (57) ABSTRACT

Medical system comprising a hollow catheter 14, for insertion into a human or animal body, and an elongated x-ray tube unit 12 provided with an x-ray tube 16 at its distal end and adapted to be inserted into the catheter. A distal pole 8 of the x-ray tube is connectable to a connection means 22 in said catheter, wherein the x-ray tube is energised via a single electrical conductor 18 in said x-ray tube unit connected to the proximal pole and via said connection means.

21 Claims, 5 Drawing Sheets

MEDICAL DEVICE

FIELD OF THE INVENTION

The present invention relates to a medical system, a method of using the system, an elongated, electrically activated x-ray tube unit and a hollow catheter according to the preambles of the independent claims.

In general the present invention relates to connecting a miniature x-ray tube for in vivo use to an electrical power source. A miniature x-ray tube according to the invention is, for example, useful in applications for prevention of restenosis and for treating diseases, such as cancer, in a living body.

BACKGROUND OF THE INVENTION

In treating stenosis in coronary arteries, a restenosis occurs in 30–60% of the cases. It is known that a treatment with beta- or gamma- (x-ray) radiation will decrease the occurrence of restenosis substantially.

Another example of an application of the present invention is treatment of cancer tumors where it is desired to deliver radiation locally.

Methods to apply the radiation to the site of treatment are presently subject to intensive research. Generally, a hollow catheter is inserted into the body, typically via an artery, in such a way that its distal end is placed near the site of treatment. A source of radiation attached to the distal end of an elongated member is inserted into the hollow catheter, and is forwarded until the radiation source is disposed at a proper position for radiating the site of treatment. In the specific case of treating cardiac vessels, the catheter is placed near the cardiac vessel tree (this catheter often called a "guide catheter"). A very thin wire—called guide wire—is then used to probe further and reach the site where treatment shall be performed. The therapeutic device is moved along this wire, i.e. by threading the device onto the guide wire. It obvious that the therapeutic device has to have a hole close to its distal end in order to do this.

For example, the use of radioactive pellets or balloons etc. as radiation source is known. Since this method has some drawbacks, such as the need for substantial efforts to control radiation in the environment outside the patient, the use of a miniature electrical x-ray tube including a cold cathode has been proposed. Such a tube may be switched on and off due to its electrical activation. An example of such a x-ray tube is described in the U.S. Pat. No. 5,854,822.

Figure 1:
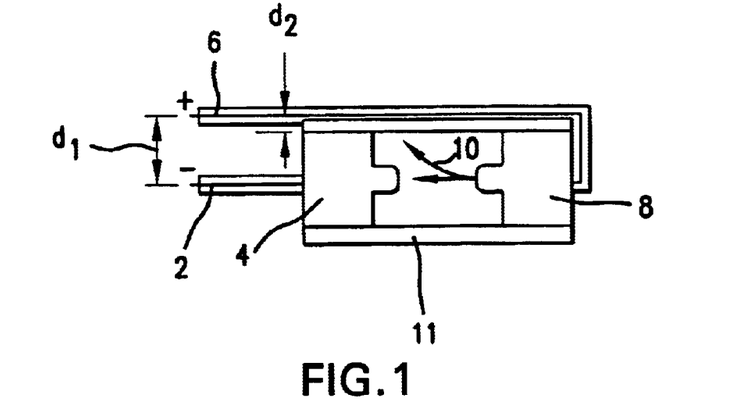
FIG. 1 is a cross-sectional view of a miniature x-ray tube illustrating the prior art.

A conventional miniature electrical x-ray tube requires electrical conductors to connect the tube, i.e. its anode and cathode, to an external power supply. Conventionally, two conductors, one for the cathode and one for the anode of the tube are connected to the tube. FIG. 1 schematically illustrates an x-ray tube according to this prior art. One of the conductors 2 is connected to one of the electrodes, e.g. the anode 4, and the other conductor 6 is connected to the other electrode, e.g. the cathode 8. The distance between the conductors is approximately the same as the radius of the x-ray tube and a breakdown might occur if the used voltage is increased. The breakdown may also occur between the electrode 4 and the conductor 6. However, due to the small dimensions used, the outer diameter of the connecting cable is typically in the range of 1–5 mm when used for cancer treatment and less than 1.5 mm when used in cardiology, and the high voltages used, typically 20 kV, the probability for electrical breakdown between the connections to the tube is considerable. In FIG. 1 "d1" designates the distance between the conductors, and the distance "d2" designates the distance between the electrode 4 and the conductor 6.

The prior art device has to be sufficiently small to be able to enter for instance cardiac vessels. The maximum dimension in this case should be <2 mm in diameter, preferably 1.5 mm in diameter. The breakdown over d2 is determined by the electrical properties of the insulating tube 11 that mechanically connects the two electrodes to each other and the distance between the electrode 4 and the conductor 6. The voltage applied over the electrodes should be some 20 kV in order to achieve radiation energies that are penetrating far enough into the body tissue to be treated. Further more, a safety margin must be applied, and therefore the design should be made so that one safely can apply say 30 kV over the distances d1 and d2.

There are few materials considered for the insulating tube wall 11 that could withstand the voltage needed. The tube wall material should also be impervious to gas diffusion, so that the vacuum needed inside the tube is maintained over a long period of time. Pyrolytic Boron Nitride (pBN) is described as a good choice, having reported breakdown voltages of some 200 kv/mm. However pBN is relatively brittle and may easily break. A mechanically stronger choice is Alumina, which has the drawback of having only 40 kV/mm breakdown. If Alumina is used in prior art configurations, the dimension must be increased to achieve the safety margin and thus the preferred diameter of 1.5 mm or less is hard to achieve.

FIG. 1 also illustrates the deflection of the electron beam 10 due to the vicinity to the other conductor 6 in a principal manner. The outer conductor 6 typically has a coaxial geometry.

WO-98/48899 relates to a miniature X-ray unit using a coaxial cable to connect the x-ray tube to the power source. This means that the distance corresponding to the x-ray tube radius, together with the dielectric medium between the conductors, or electrode to conductor, is limiting for the voltage level that can be applied across the electrodes.

Therefore, there is a need for a novel way to connect an x-ray tube to a power source, designed to allow for higher voltage potential levels.

It is an object of the present invention to provide a device and a method for electrically connecting a miniature electrical x-ray tube to an external power source, allowing for improved voltage potential levels to be delivered to the x-ray tube, without having to increase the geometry and giving a wider choice of materials for the design of the miniature x-ray source be used that can improve the mechanical strength.

SUMMARY OF THE INVENTION

The above-mentioned object is obtained by a medical system, a method of using the system, an elongated x-ray tube unit and a hollow catheter according to the characterizing portions of the independent claims.

Preferred embodiments are set forth in the dependent claims.

Generally, according to the invention one of the conductors for supplying voltage to the x-ray tube is integrated with, or attached to, the hollow catheter used to provide a path for inserting the x-ray source. At the distal end of the hollow catheter, said conductor is exposed at the inside of the hollow catheter to exhibit a terminal surface. The electrical connection to the x-ray tube is at one end (the proximal end when inserted into the hollow catheter) connected to a single electric cable, while the other end (the distal end when inserted into the hollow catheter) is provided with a terminal end surface adapted to achieve an electrical connection to the terminal surface of the hollow catheter when completely inserted into said catheter.

A great advantage of the present invention according to the claims is that the x-ray tube unit with the radiation source need not be sterilized because it is inserted into the hollow catheter that has an open proximal end to receive the tube unit and a closed distal end. Therefore only the catheter needs to be sterilized in that the x-ray tube unit is never in contact with body tissue. Thus, x-ray tube unit itself may be reused without sterilization. This should be compared with prior art systems where the insertion catheter (or guide catheter) has an open distal end and where the radiation source unit is in contact with body tissue.

Another great advantage of the present invention is that, if, due to unforeseeable circumstances any part of or the whole x-ray tube is damaged in any way, no parts would be spread inside the body but would instead be kept inside the hollow catheter.

In a specific embodiment of the invention, a radiation shielding material is provided at or in the hollow catheter. The shielding material is selected to absorb radiation of lower energies to a higher extent than radiation of higher energies.

DETAILED DESCRIPTION OF EMBODIMENTS

Figure 2:
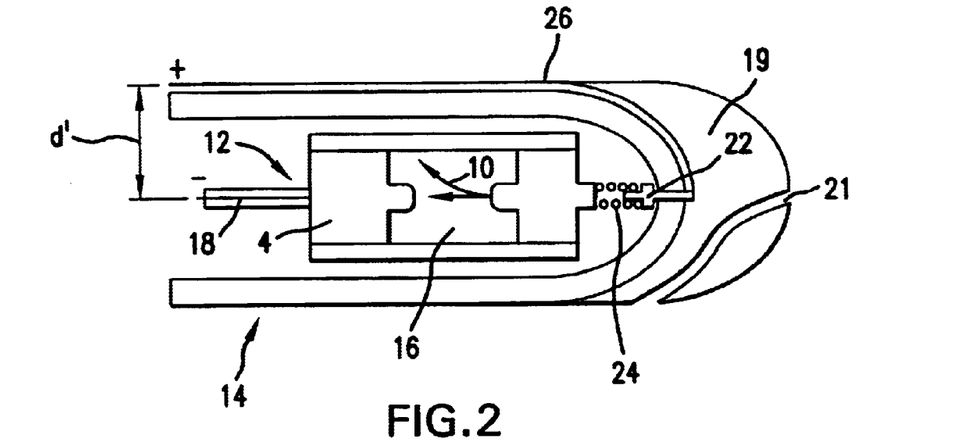
FIG. 2 is a schematic cross-sectional view of a first embodiment of a medical system according to the present invention.

FIG. 2 is a schematic cross-sectional view of a first embodiment of a medical system according to the present invention. The medical system illustrated in FIG. 2 comprises an x-ray tube unit 12 inserted into a hollow catheter 14. The x-ray tube unit includes an x-ray tube 16, a conductor 18 and an external contact arrangement (not shown). FIG. 2 only shows the distal parts of the system. The x-ray tube unit comprises the x-ray tube 16 provided with a distal pole 8 and a proximal pole 4. The proximal pole 4 is connected to a power source (not shown) via an electrical conductor 18. The distal pole 8 is electrically accessible at the outside of the distal end of the unit. In FIG. 2 this is illustrated as a protrusion of the distal pole. Also shown in FIG. 2 is a typical extension 19 of the catheter with a hole 21 to allow the device to be threaded over the guide wire as mentioned above. Many different types of guiding extensions are described in the prior art that may be applied on a catheter according to the present invention. Since the present invention may be used with any type of guiding extension or even without an extension and because the type of extension used is not directly related to the present invention it is not further described herein.

The x-ray tube may have a cylindrical outer shape. However, other shapes are naturally possible without departing from the scope of the invention as defined in the appended claims.

The hollow catheter is typically made of a plastic material. Examples of plastics that are usable, alone or in combinations, are Teflon, Polyimides, polyethylene etc., that all have high electrical breakdown characteristic. In some of the embodiments it is important to ensure a high electrical breakdown for regulatory safety reasons. For instance, Ultrahigh molecular polyethylene can be manufactured in sufficiently thin layers with a very high dielectric strength, 15 000V/mil according to the vendor, AREMCO Products, Valley Cottage, N.Y., USA.

The hollow catheter 14 is provided with a connection means 22 accessible at the inner surface of the distal end side of the hollow catheter and adapted to be connected to the distal pole of the x-ray tube. The connection means 22 includes a helix-formed spring means 24 that is slightly compressed when the x-ray tube unit is fully inserted into the hollow catheter in order to secure safe electrical connection between the connection means and the distal pole. Any means adapted to secure safe electrical connection performed by the spring means 24 may naturally be used instead of the spring means. The helix-formed spring means may be replaced by e.g. any kind of leaf spring.

During insertion of the of the x-ray tube unit 12 into the catheter a force is applied on the conductor 18 and its electrically insulating tubing of the x-ray tube unit 12 in the longitudinal direction of the catheter.

The use of the hollow catheter allows the system design to be made so that the x-ray tube wall material takes up only a fraction of the voltage required, and the catheter plastic material takes up the remaining part, so the overall requirement of e.g. 30 kV is met. As an example, a 0.2 mm Alumina tube wall a 9 mil (0.23 mm) catheter wall of ultrahigh molecular polyethylene will be able to withstand some 140 kV, simply meaning that the breakdown will not occur at this point. Taking a gap between the tube wall and the x-ray tube into account of 0.2 mm the above radius would add up to 0.63 mm, giving enough space left for conductors etc. to meet the target dimension of 1.5 mm, and in fact allowing for further miniaturisation.

Hence, materials for the x-ray tube unit design need not be optimised on their dielectric properties in the same manner as described in prior art.

The connection means is electrically connected to at least one insulated electrical conductor 26 arranged outside an outer wall and running in a longitudinal direction of the catheter. The proximal end of the electrical conductor 26 is connected to the power source (not shown).

According to a refined embodiment of the invention the catheter is provided with one or many x-ray radiation opaque markings making it possible to localise the catheter by using conventional x-ray imaging technique.

Figure 3:
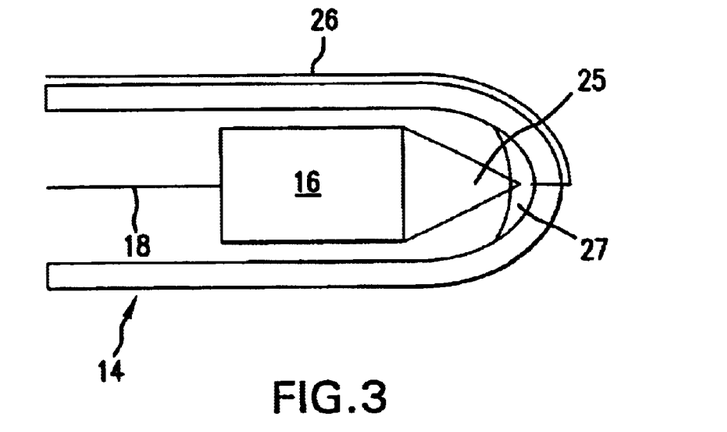
FIG. 3 illustrates an alternative embodiment of the connection means according to the invention.

FIG. 3 illustrates schematically an alternative embodiment of the connection means 22. In order to ensure electrical connection a pointed tip 25 is arranged at the distal end 8 of the x-ray tube 16. When contact is to be established the tip, preferably made of a relatively hard material, e.g. Tungsten, is pressed into a soft material 27 (e.g. Al, Au) on the inside of the catheter. The tip has a curvature large enough to ensure that the catheter is not punctured. A benefit wvith this embodiment is that the tip and the x-ray tube electrode can be made in one piece, and thus resulting in a simplified manufacturing.

Prior use it is important to ensure that electrical connection has been established between the distal pole of the x-ray tube and the connection means of the catheter. This check may be performed in many different ways. Often combinations of mechanical and electrical methods are used. According to one example first a mechanical connection is established and then a predetermined electrical activation pattern is used (e.g. a ramp) and evaluated. Doing so it is advantageous to take the exponential behaviour of the current through the cold cathode x-ray tube into account. The current follows the well-known Fowler-Nordheim relation $I=KV^2 e^{(-b/V)}$ where V is the applied voltage and K and b are constants.

In the method to check for contact, a much smaller voltage is applied (e.g. 5 kV) and the current is compared with a known value. If the tube is designed to have a current of 10 microamperes at 20 kV the current at 5 kV may typically be in the order of nA ($10^{-9}$A).

Figure 4:
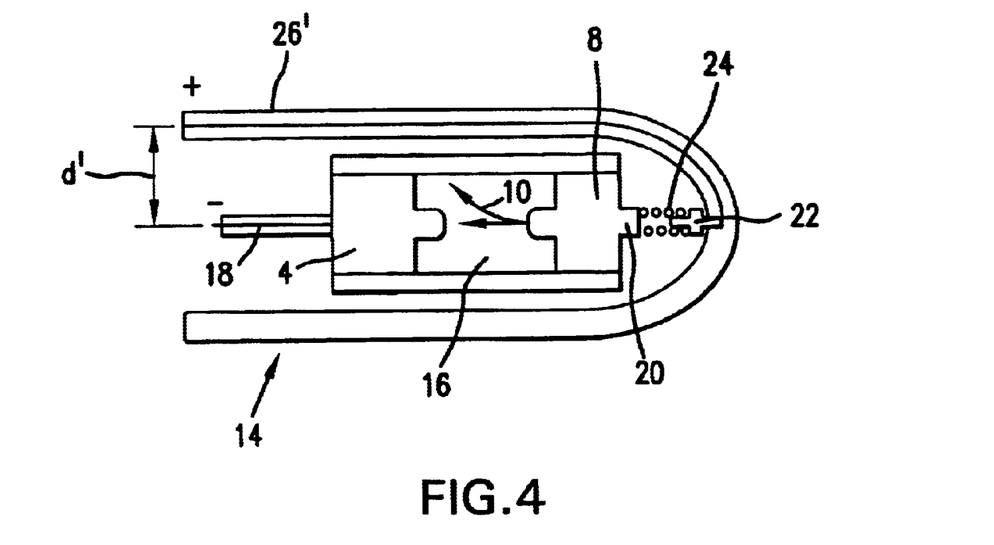
FIG. 4 is a schematic cross-sectional view of a second embodiment of a medical system according to the present invention.

FIG. 4 is a schematic cross-sectional view of a second embodiment of a medical system according to the present invention. The second embodiment illustrated in FIG. 4 differs from the first embodiment shown in FIG. 2 only in that the electrical conductor 26' connecting the connection means 22 to the power source (not shown) according to this embodiment is integrated into the catheter wall, electrically isolated from the outside, and running in a longitudinal direction of said catheter. Apart from this difference the second embodiment is identical to the first embodiment and the same reference signs and description, e.g. regarding different ways to arrange the connection means, as in the first embodiment apply also for the second embodiment.

Figure 5:
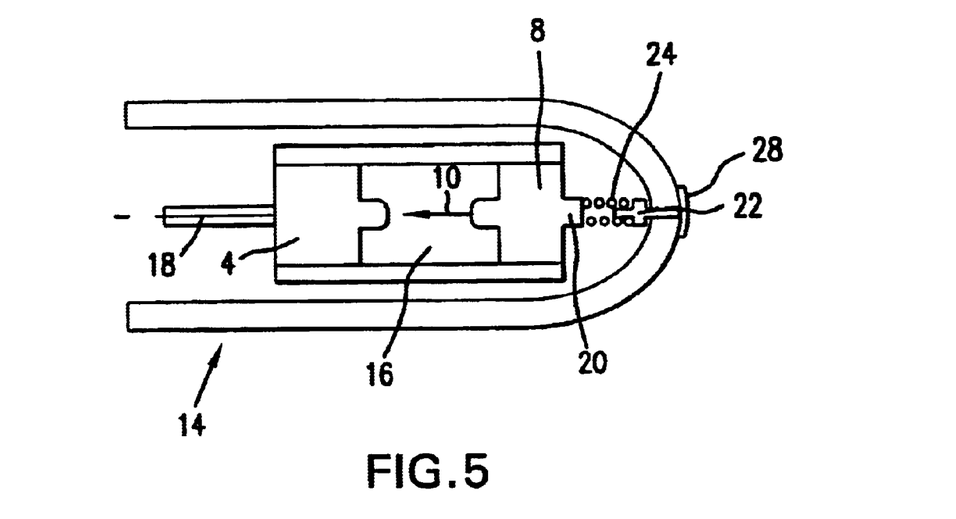
FIG. 5 is a schematic cross-sectional view of a third embodiment of a medical system according to the present invention.

FIG. 5 is a schematic cross-sectional view of a third embodiment of a medical system according to the present invention. In this third embodiment of the invention the connection means 22 is exposed to tissue outside the catheter, and the electrical connection between connection means and the power source (not shown) is achieved between the exposed connection 28 and a tissue electrode (not shown). In this embodiment the tissue is used as a conductive electrical path. In order to eliminate any possibilities of tissue stimulation in the vicinity of the exposed connection 28 the used electrical current is below 10 $\mu$A. Stimulation pulses that are used by pacemakers have a current in the range of mA.

The current has to be kept under for example 10 $\mu$A (depending somewhat on the tube design) also in order to avoid excessive heating if no active way of cooling the miniature x-ray tube is used.

Apart from this difference the third embodiment is identical to the first embodiment and the same reference signs and description, e.g. regarding different ways to arrange the connection means, as in the first embodiment apply also for the third embodiment.

Figure 6:
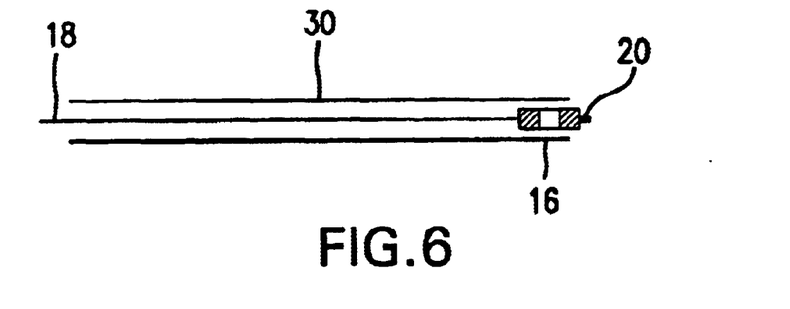
FIG. 6 is a schematic cross-sectional view of a x-ray tube unit according to the present invention.

FIG. 6 is a schematic cross-sectional view of a x-ray tube unit according to the present invention. The x-ray tube 16 is arranged at the distal end and provided with the distal pole 8 that is electrically accessible at the distal end of the unit, e.g. via the protrusion 20. The single electrical conductor 18 connected to the proximal pole 4 is also disclosed. An electrically insulating outer sheet extending along the whole length of the x-ray tube unit is also schematically illustrated.

Figure 7:
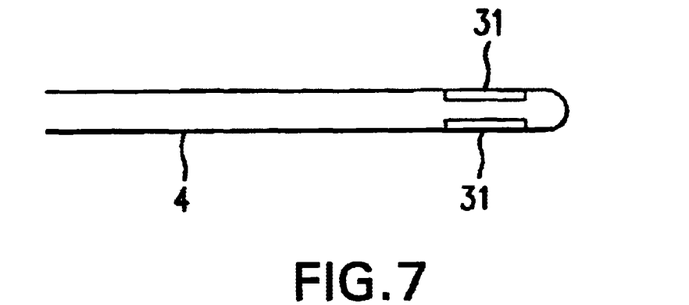
FIG. 7 is a schematic illustration of a hollow catheter according to an alternative embodiment of the present invention.
Figure 8:
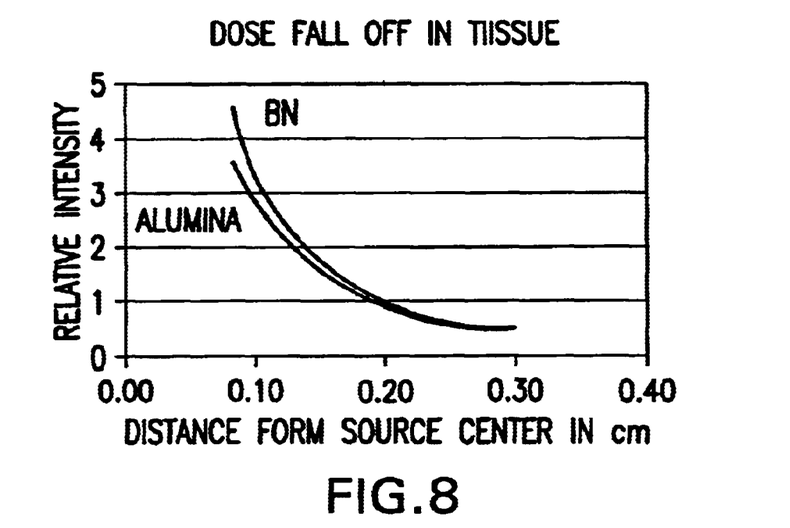
FIG. 8 is a curve showing the typical dose fall off from an x-ray tube according to a preferred embodiment of the invention.

FIG. 7 is a schematic illustration of a hollow catheter according to an alternative embodiment of the present invention. According to this embodiment is a shielding means 31 arranged so that x-ray radiation generated by the x-ray tube is shielded according to a predetermined radiation pattern. In treating cardiac vessels to prevent restenosis, a commonly prescribed dose is typically 15 Gy to be delivered 2 mm from the radiation source. Due to the exponential decrease in intensity, as well as the cylindrical symmetry of the vessel, a much higher dose will be delivered adjacent to the radiation source. For an electrical x-ray tube that sends out Brehms-strahlung this is further emphasised because the lower energy photons will not penetrate as deep as the high-energy photons. It is therefore important to keep the dose delivered in close proximity to the x-ray source as near as possible to the prescribed dose to be delivered 2 mm from the source. FIG. 8 shows the typical dose fall off from an x-ray tube in a Teflon catheter. The dose distribution has been normalised to the point of interest, which is the point the prescribed dose is related to, e.g. 2 mm from the source (used in this case). For this example, the wall thickness of the tube is 200 micrometers, the tube wall material is Alumina ($Al_2O_3$) and Boron Nitride respectively and the thickness of the catheter is 250 um. As can be seen from this figure, the dose is 3–5 times higher in the tissue closest to the catheter. The shielding means and the conductor are preferably made as one physical part, and the material and thickness of the conductor is therefore chosen so that the shielding criteria are met according to the below discussion.

The shielding means is arranged on the outer surface or integrated into the wall of the hollow catheter. The shielding material is selected to absorb radiation of lower energies to a higher extent than radiation of higher energies. The shielding means is preferably a thin metal foil, and also acts as the conductor.

The transmission of radiation through a foil can be described by the well-known equation:

$$I(x) = I_0 \exp(-x\mu/\rho)$$

where $I_0$ is the incident radiation intensity, x is the distance into the foil (e.g. in cm) and $\mu$ is the energy dependent attenuation coefficient in $cm^2/g$ and $\rho$ is the density of the material. Values for $\mu$ are readily obtained from the National Institute of Standards and Technology, for example. Values for $\rho$ are obtained from any standard handbook of physics.

A typical thickness value should be in the range of 0.01 micrometers to 100 micrometers in order to be practical, the specific value depending on material and method of deposition/attachment. For instance, an evaporated layer is usually made in the thinner range, and an electrochemical deposition or a foil in the thicker part of the range.

The shielding material and thickness is chosen from the criteria that a) as much as possible of higher radiation should be transmitted b) as little as possible of lower energy should be transmitted c) take absorption edges into account in the range 7 keV–10 keV d) The thickness chosen from a) and b) should be practical; it must not add too much mechanical thickness and stiffness and should be easy to combine into the catheter.

e) The material of the foil should preferably be non-toxic.

f) The material should be electrically conducting according to a preferred embodiment of this invention.

TABLE 1

| Element | Z | Thickness for 90% transmission of 15 keV photons | Transmission ratio I(E)/I(15 keV) | | |
|---|---|---|---|---|---|
| | | | E = 10 keV | E = 8 keV | E = 5 keV |
| Al | 13 | 50 um | 78% | 56% | 8% |
| Si | 14 | 45 um | 78% | 56% | 9% |
| Ti | 22 | 6.5 um | 82% | 61% | 15% |
| V | 23 | 4.5 um | 80% | 62% | 32% |
| Cr | 24 | 3.5 um | 79% | 60% | 30% |
| Fe | 26 | 2.5 um | 80% | 61% | 85% |
| Ni | 28 | 1.7 um | 81% | 68% | 85% |
| Cu | 29 | 1.5 um | 84% | 83% | 61% |
| Pd | 46 | 2.5 um | 81% | 63% | 16% |
| Ag | 47 | 2.5 um | 81% | 63% | 16% |
| W | 74 | 0.4 um | 104% | 98% | 73% |
| Au | 79 | 0.3 um | 103% | 98% | 75% |

In table 1 a number of elements are listed. For each element the material data has been used and the ratio between high and low energy transmission is given together with the thickness that transmits 90% of the higher energy radiation. Energies below 5 kV do not penetrate the x-ray tube wall to any large extent and are considered relatively unimportant. Here, the assumptions have been that as much as possible of 15 kV radiation should be transmitted and as little as possible of radiation less than 8 kV should be transmitted. It is obvious that the exact values are not limiting the scope of the invention. Table 1 will be a first indicator on how to choose material for the shield. In order to properly design the shield thickness and to choose the shield material the material of the tube must be taken into account. Two commonly used materials are pyrolytic Boron Nitride and Alumina. The former will transmit relatively low energy radiation as compared to the latter. The shielding function will therefore be of more pronounced importance when using BN as compared to Alumina. Also important is that, when adding shielding material, the dose rate in general will decrease and the treatment time will be prolonged. Therefore the reduction of high dose in the near tissue will result in an overall longer time. There are therefore practical limits to what can be achieved. As seen from Table 1., the lighter elements have the benefit of acting as better shields with the drawback that they must be made thicker. Examples on preferred materials for this application are the metals that transmit relatively good at 10 kV but little at 5 kV: The elements with atomic numbers 21 through 50 have the best properties according to the above criteria. Also some of the lighter elements, such as Aluminum are usable. Heavy elements, such as Gold are also usable, all depending on the combination with the vacuum tube material. In using Boron Nitride for instance, low energy photons are transmitted to a larger account as compared to Alumina ($Al_2O_3$). In this case it becomes more important to provide a shield for low energy photons. When performing this more accurate analysis, it is important to take the actual physical geometry into account as detailed as possible.

Figure 9A:
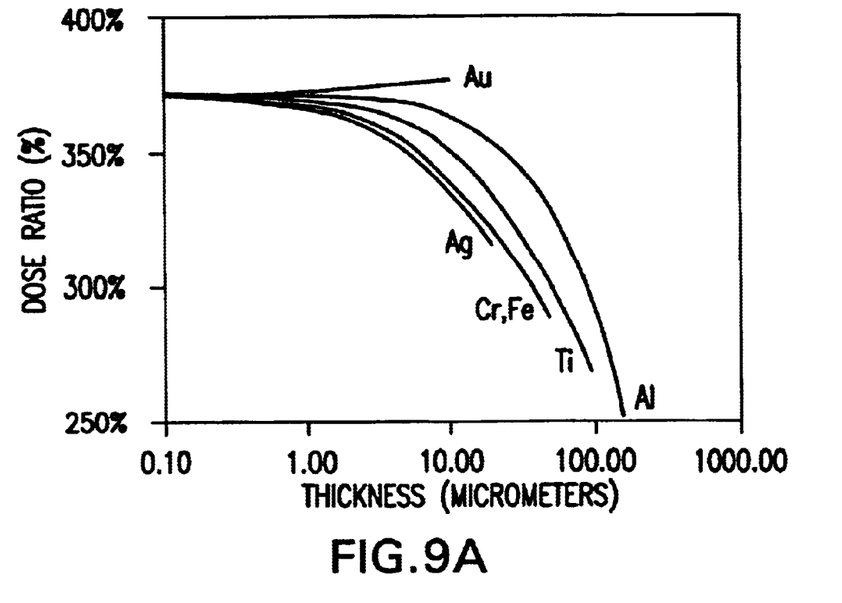
FIGS. 9a and 9b show, respectively, the dose relative to the radiation dose at 2 mm plotted as a function of shield material thickness for various materials.
Figure 9B:
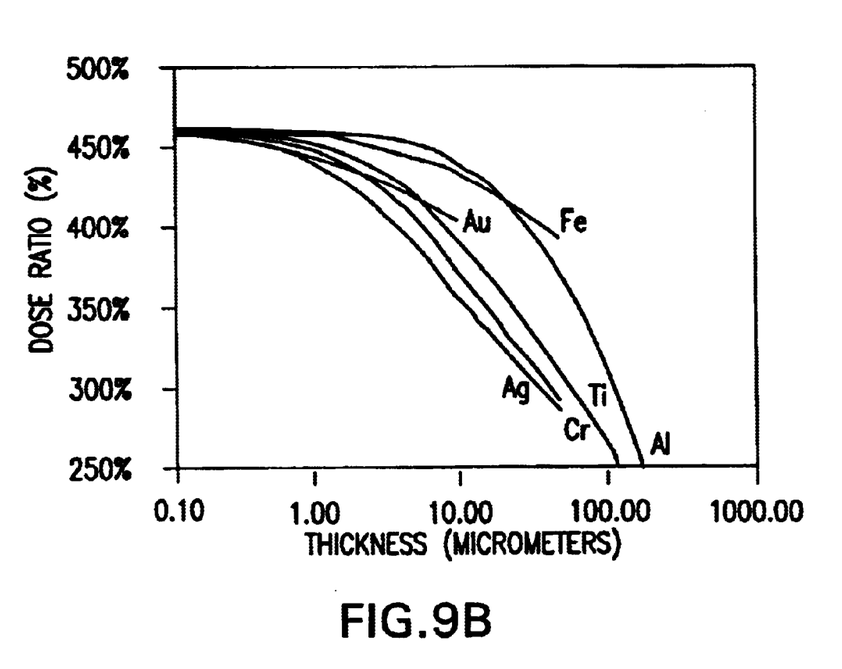

In FIGS. 9a and 9b respectively, the dose relative to the dose at 2 mm are plotted as a function of shield material thickness for various materials. FIG. 9a shows an Alumina x-ray tube and 9b a Boron Nitride tube. As can be seen the lighter elements (e.g. Al) are the best in reducing the dose close to the tube, but the penalty is the thickness. In any case a reduction to approx. 2.5 times is feasible.

Table 2 shows a comparison of various shield materials and their resulting thickness (t) and the dose ration between the dose delivered to the tissue just outside the x-ray device and the prescribed dose (15 Gy @ 2 mm) under the condition that the total treatment of 30 mm stenosis shall take 30 minutes. The table shows values for both Alumina (Al203) and Boron Nitride (BN)

TABLE 2

| | Ceramic in X-ray Tube | | | |
|---|---|---|---|---|
| | Alumina | | BN | |
| Shield Material | t ($\mu$m) | Dose Ratio | t ($\mu$m) | Dose Ratio |
| Ag | 8.1 | 339% | 15 | 338% |
| Al | 181 | 245% | 331 | 197% |
| Au | 1.7 | 373% | 3.8 | 425% |
| Cr | 10.4 | 338% | 19.4 | 338% |

TABLE 2-continued

| | Ceramic in X-ray Tube | | | |
|---|---|---|---|---|
| | Alumina | | BN | |
| Shield Material | t (μm) | Dose Ratio | t (μm) | Dose Ratio |
| Fe | 7.6 | 344% | 14.8 | 427% |
| Si | 155 | 255% | 282 | 210% |
| Ti | 21.5 | 332% | 40.4 | 320% |
| Y | 32.3 | 326% | 32.3 | 326% |
| Zr | 20.3 | 335% | 38.5 | 326% |

However, for applications where space is limited, as thick layers as 200 μm cannot be used. If the thickness is limited to for example 50 micrometers the results are shown in table 3. From this table the deduction is that a Ti layer or tube with a thickness of 40 μm would be good choice. Other preferred materials are would be Y, Zr for example. For Alumina tubes the choice would be Y, Si, Al and possibly Ti.

TABLE 3

| | Ceramic in X-ray Tube | | | |
|---|---|---|---|---|
| | Alumina | | BN | |
| Shield Material | t (μm) | Dose Ratio | t (μm) | Dose Ratio |
| Ag | 8.1 | 339% | 15 | 338% |
| Al | 50 | 328% | 50 | 370% |
| Au | 1.7 | 373% | 3.8 | 425% |
| Cr | 10.4 | 338% | 19.4 | 338% |
| Fe | 7.6 | 344% | 14.8 | 427% |
| Si | 50 | 327% | 50 | 366% |
| Ti | 21.5 | 332% | 40.4 | 320% |
| Y | 32.3 | 326% | 32.3 | 326% |
| Zr | 20.3 | 335% | 38.5 | 326% |

It should be noted that, if the geometry is changed, this optimization must be redone. The materials choices will not be influenced to a large extent, but the optimum thickness will. Also, other criteria, such as maximum shield thickness, will yield other optimum configurations.

According to refined embodiments of the first and second preferred embodiments described above the electrical conductor 26, 26' also functions as shielding means.

Figure 10:
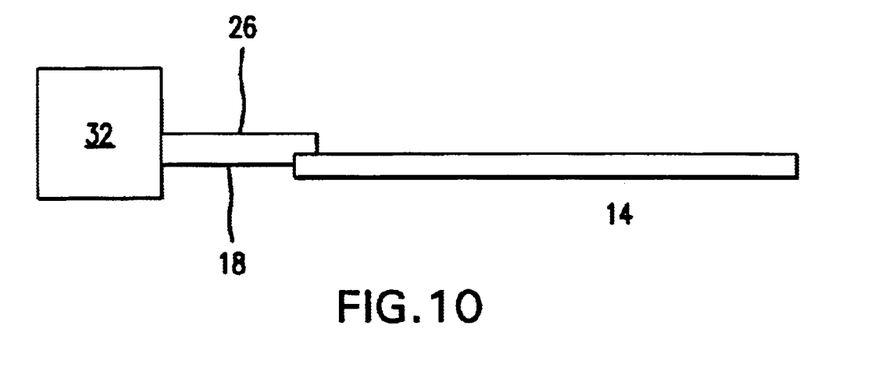
FIG. 10 is block diagram of the medical system according to the first or second embodiment of the present invention.

FIG. 10 is block diagram of the medical system according to the first or second embodiment of the present invention. The medical system may also comprises a control device 32 including i.e. a power source connected to the electrical conductor 18 of the x-ray tube unit and to the electrical conductor arranged at the hollow catheter 14.

Figure 11:
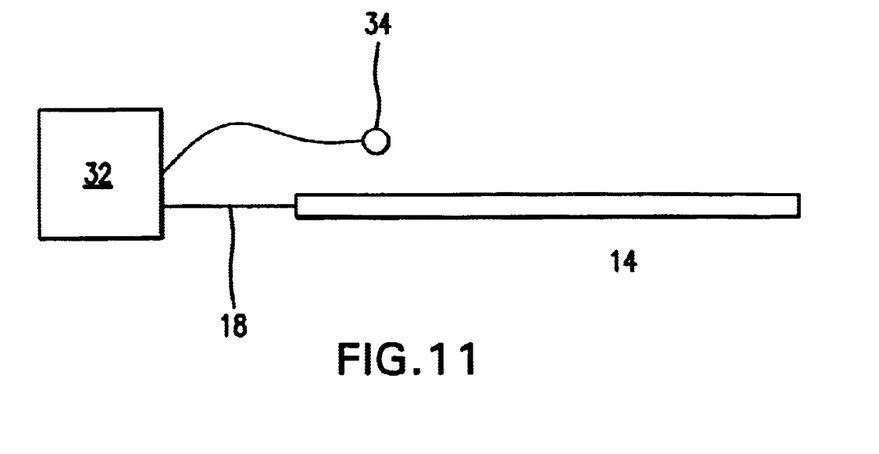
FIG. 11 is block diagram of the medical system according to the third embodiment of the present invention.

FIG. 11 is block diagram of the medical system according to the third embodiment of the present invention. The medical system comprises the control device 32 including i.e. a power source connected to the electrical conductor 18 of the x-ray tube unit. The other electrical connection from the power source is connected to a tissue electrode 34 that is e.g. a patch electrode applied at the skin of a patient.

The control device 32 including the power source to energise the x-ray tube may also comprise a checking means adapted to check that electrical connection is established between the distal pole of the x-ray tube and the connection means. The checking is performed e.g. by applying a predetermined low voltage on the x-ray tube, measuring the corresponding current and comparing the measured current with a threshold value indicating established electrical connection.

Of course, several modifications of an x-ray tube according to the inventions are possible. For example the x-ray tube could include grids, well known in themselves, to form a triode.

The present invention is not limited to the above-described preferred embodiments. Various alternatives, modifications and equivalents may be used. Therefore, the above embodiments should not be taken as limiting the scope of the invention, which is defined by the appending claims.

What is claimed is:

1. Medical system comprising a hollow catheter (14) having an open proximal end and a closed distal end, for insertion into a human or animal body, and an elongated x-ray tube unit (12) provided with an x-ray tube (16) at its distal end and adapted to be inserted into the catheter, a distal pole (8) of the x-ray tube is connectable to a connection means (22) in the distal end of said catheter, wherein the x-ray tube is energised via a single electrical conductor (18) in said x-ray tube unit connected to a proximal pole (4) of said x-ray tube and via said connection means.

2. Medical system according to claim 1, characterized in that the system comprises a control device (32) including a power source to energise the x-ray tube and a checking means adapted to check that electrical connection is established between the distal pole of the x-ray tube and the connection means wherein said checking is performed by applying a predetermined low voltage on the x-ray tube, measuring the corresponding current and comparing the measured current with a threshold value indicating established electrical connection.

3. Elongated X-ray tube unit (12) comprising an x-ray tube (16) at the distal end, the x-ray tube includes at least one distal pole (8) and one proximal pole (4), said unit is provided with a single electrical conductor (18) connected to the proximal pole and the distal pole is adapted to be electrically accessible at a closed end of a catheter at the distal end of the unit.

4. X-ray tube unit according to claim 3, characterized in that an accessible part of the distal pole is in the form of a protrusion.

5. X-ray tube unit according to claim 4, characterized in that the accessible part of the distal pole is a pointed tip (25).

6. X-ray tube unit according to claim 3, characterized in that the accessible part of the distal pole and an active part of the distal pole in the x-ray tube is made in one unitary piece (26).

7. X-ray tube unit according to claim 3, characterized in that said poles are alternately anode and cathode, respectively.

8. X-ray tube unit according to claim 3, characterized in that said distal pole is an anode and said proximal pole is a cathode.

9. X-ray tube unit according to claim 3, characterized in that said distal pole is a cathode and said proximal pole is an anode.

10. Hollow elongated catheter, characterized in that said catheter is adapted to receive an elongated x-ray tube unit according to any of claims 3–9 and provided with a connecting means (22) that is connectable to the distal pole of the x-ray tube unit, wherein the x-ray tube is energised via said single electrical conductor connected to the proximal pole of the x-ray tube and via said connection means.

11. Hollow elongated catheter according to claim 10, characterized in that said catheter has an open proximal end where the x-ray tube is received and a closed distal end where the connection means is arranged.

12. Hollow elongated catheter according to claim 10, characterized in that said connection means is electrically connected to at least one electrical cable integrated in an outer wall and running in a longitudinal direction of said catheter.

13. Hollow catheter according to claim 10, characterized in that said connection means is electrically connected to at least one electrical cable arranged outside an outer wall and running in a longitudinal direction of said catheter.

14. Hollow catheter according to claim 10, characterized in that said connection means is exposed to tissue outside said catheter, wherein the electrical connection is achieved between said exposed connection and a tissue electrode.

15. Hollow catheter according to claim 10, characterized in that said catheter is provided with shielding means arranged so that x-ray radiation generated by said x-ray tube is shielded according to a predetermined radiation pattern.

16. Hollow catheter according to claim 15, characterized in that said shielding means is a metal foil.

17. Hollow catheter according to claim 16, characterized in that the metal used is one of Al, Ti, V, Ni, Cr, Fe, Pd, or alloys of these, e.g. stainless steel.

18. Hollow catheter according to claim 10, characterized in that a distal end of the catheter is provided with an extension (19) with a hole (21) to allow the catheter to be guided along a guide wire.

19. Hollow catheter according to claim 10, characterized in that the catheter is provided with one or many x-ray radiation opaque markings.

20. Method of using a medical system comprising a hollow catheter (14) having an open proximal end and a closed distal end, for insertion into a human or animal body, and an elongated x-ray tube unit (12) provided with an x-ray tube (16) at its distal end and adapted to be inserted into the catheter, a distal pole (8) of the x-ray tube is connectable to a connection means (22) in the distal end of said catheter, wherein the x-ray tube is energised via a single electrical conductor (18) in said x-ray tube unit connected to a proximal pole (4) of said x-ray tube and via said connection means, wherein the method comprises the following steps:

A) inserting said hollow catheter having an open proximal end and a closed distal end into a body so that the distal end of the catheter is arranged a predetermined distance distal a position where x-ray radiation treatment is to be performed;

B) inserting said elongated x-ray tube unit (12) into the catheter to a position where the distal pole (8) of the x-ray tube is connected to the connection means (22) of said catheter, and C) moving, according to a pre-set movement pattern, the hollow catheter and the x-ray tube unit so that a predetermined dose of radiation generated by the activated x-ray tube is applied to the treatment site.

21. Method according to claim 20, characterized in that the insertion in step B) is performed by applying a force on the conductor (18) and its electrically insulating tubing of the x-ray tube unit (12) in the longitudinal direction of the catheter.

* * * * *